(12) United States Patent
Shimizu et al.

(10) Patent No.: US 12,239,619 B2
(45) Date of Patent: Mar. 4, 2025

(54) **COMPOSITION FOR INDUCING PILI FORMATION IN BACTERIUM OF GENUS *BIFIDOBACTERIUM***

(71) Applicants: MORINAGA MILK INDUSTRY CO., LTD., Tokyo (JP); NATIONAL UNIVERSITY CORPORATION KOBE UNIVERSITY, Hyogo (JP); THE KITASATO INSTITUTE, Tokyo (JP)

(72) Inventors: Kanetada Shimizu, Kanagawa (JP); Ro Osawa, Hyogo (JP); Keita Nishiyama, Kanagawa (JP); Nobuhiko Okada, Kanagawa (JP); Nobuhiro Koyama, Kanagawa (JP); Takao Mukai, Kanagawa (JP); Hiroshi Tomoda, Kanagawa (JP)

(73) Assignees: Morinaga Milk Industry Co., Ltd., Tokyo (JP); National University Corporation Kobe University, Hyogo (JP); The Kitasato Institute, Tokyo (JP)

( * ) Notice: Subject to any disclaimer, the term of this patent is extended or adjusted under 35 U.S.C. 154(b) by 0 days.

(21) Appl. No.: 17/433,755

(22) PCT Filed: Feb. 28, 2020

(86) PCT No.: PCT/JP2020/008457
§ 371 (c)(1),
(2) Date: Aug. 25, 2021

(87) PCT Pub. No.: WO2020/175690
PCT Pub. Date: Sep. 3, 2020

(65) Prior Publication Data
US 2022/0133665 A1    May 5, 2022

(30) Foreign Application Priority Data
Feb. 28, 2019 (JP) ................. 2019-036309

(51) Int. Cl.
*A61K 31/192* (2006.01)
*A23K 10/18* (2016.01)
(Continued)

(52) U.S. Cl.
CPC ............ *A61K 31/192* (2013.01); *A23K 10/18* (2016.05); *A23K 20/111* (2016.05); *A23L 2/52* (2013.01);
(Continued)

(58) Field of Classification Search
CPC .. A61K 31/192; A61K 35/742; A61K 35/745; A61K 2035/115; A23K 10/18;
(Continued)

(56) References Cited

U.S. PATENT DOCUMENTS

2018/0168196 A1    6/2018    Middleton et al.

FOREIGN PATENT DOCUMENTS

| JP | 63-79586 A | 4/1988 |
| JP | 2013-078284 A | 5/2013 |
| KR | 20170017176 A * | 2/2017 |

OTHER PUBLICATIONS

Parkar, Shanthi G., David E. Stevenson, and Margot A. Skinner. "The potential influence of fruit polyphenols on colonic microflora and human gut health." International journal of food microbiology 124.3 (2008): 295-298. (Year: 2008).*

(Continued)

*Primary Examiner* — Louise W Humphrey
*Assistant Examiner* — Candice Lee Swift
(74) *Attorney, Agent, or Firm* — Cermak & McGowan LLP; Shelly Guest Cermak

(57) ABSTRACT

The object is to provide a method for inducing pili formation in bacterium of genus *Bifidobacterium* and a method for (Continued)

PPA−

PPA+ promoting intestinal colonization of the bacterium. 3-Phenylpropionic acid and/or 3-(4-hydroxyphenyl)propionic acid are an active ingredient of a composition for inducing the pili formation in the bacterium of genus *Bifidobacterium* and a composition for promoting the intestinal colonization of the bacterium.

2 Claims, 6 Drawing Sheets

(51) Int. Cl.
  *A23K 20/111*    (2016.01)
  *A23L 2/52*      (2006.01)
  *A23L 33/135*    (2016.01)
  *A61K 35/00*     (2006.01)
  *A61K 35/742*    (2015.01)
  *A61K 35/745*    (2015.01)
  *A61P 1/00*      (2006.01)

(52) U.S. Cl.
  CPC .......... *A23L 33/135* (2016.08); *A61K 35/742* (2013.01); *A61K 35/745* (2013.01); *A61P 1/00* (2018.01); *A23V 2002/00* (2013.01); *A23V 2400/533* (2023.08); *A61K 2035/115* (2013.01)

(58) Field of Classification Search
  CPC ....... A23K 20/111; A23L 2/52; A23L 33/135; A61P 1/00; A23V 2002/00; A23Y 2300/55
  See application file for complete search history.

(56) References Cited

OTHER PUBLICATIONS

Parkar, Shanthi G., Tania M. Trower, and David E. Stevenson. "Fecal microbial metabolism of polyphenols and its effects on human gut microbiota." Anaerobe 23 (2013): 12-19. (Year: 2013).*

Tripathi, Prachi, et al. "Adhesion and nanomechanics of pili from the probiotic Lactobacillus rhamnosus GG." ACS nano 7.4 (2013): 3685-3697. (Year: 2013).*

Westermann, Christina, et al. "A critical evaluation of bifidobacterial adhesion to the host tissue." Frontiers in microbiology 7 (2016): 1220. (Year: 2016).*

Bubnov, Rostyslav V., et al. "Specific properties of probiotic strains: relevance and benefits for the host." EPMA Journal 9 (2018): 205-223. (Year: 2018).*

International Search Report for PCT Patent App. No. PCT/JP2020/008457 (May 12, 2020).

Fukuda, S., et al., "Bifidobacteria can protect from enteropathogenic infection through production of acetate," Nature 2011;469:543-547.

Fanning, S., et al., "Bifidobacterial surface-exopolysaccharide facilitates commensal-host interaction through immune modulation and pathogen protection," PNAS 2012;109(6):2108-2113.

Sivan, A., et al., "Commensal Bifidobacterium promotes antitumor immunity and facilitates anti-PD-L1 efficacy," Science 2015;350(6264):1084-1089.

O'Connell Motherway, M., et al., "Functional genome analysis of Bifidobacterium breve UCC2003 reveals type IVb tight adherence (Tad) pili as an essential and conserved host-colonization factor," PNAS 2011;108 (27):11217-11222.

Turroni, F., et al., "Role of sortase-dependent pili of Bifidobacterium bifidum PRL2010 in modulating bacterium-host interactions," PNAS 2013;110(27):11151-11156.

Elsden, S. R., et al., "The End Products of the Metabolism of Aromatic Amino Acids by Clostridia," Arch. Microbiol. 1976;107(3):283-288.

Extended European search report dated Nov. 3, 2022 issued in corresponding European application No. 20762963.5.

Milani, C., et al., "The First Microbial Colonizers of The Human Gut: Composition, Activities, and Health Implications of the Infant Gut Microbiota," Microbiology and Molecular Biology Reviews, vol. 81, issue 4, 2017, pp. 1-67.

Danne, C., et al., "Pili of Gram-Positive bacteria: roles in host colonization," Research in Microbiology, vol. 163, 2012, pp. 645-658.

Turroni, F., et al., "Expression of sonase-dependent pili of Bifidobactelium bifidum PRL2010 in response to environmental gut conditions," FEMS Microbiol. Lett., vol. 357, 2014, pp. 23-33.

Singh, N. et al., "Impact of Bifidobacterium bifidum MIMBb75 on mouse intestinal microorganisms," FEMS Microbiol. Ecol., vol. 85, 2013, pp. 369-375.

Carry, E., et al., "Targeted analysis of microbial generated phenolic acid metabolites derived from grape flavanols by gas chromatography-triple quadrupole mass spectroscopy," J. Pharm. Biomed. Analysis 2018;159:374-383.

Notice of Reasons for Refusal from Japanese Patent App. No. 2021-502657 (Dec. 6, 2022) with English language machine translation.

* cited by examiner

COMPOSITION FOR INDUCING PILI FORMATION IN BACTERIUM OF GENUS BIFIDOBACTERIUM

This application is a U.S. national phase filing of, and claims priority under 35 U.S.C. § 371 to, International Application No. PCT/JP2020/008457, filed Feb. 28, 2020, and claims priority therethrough under 35 U.S.C. § 119 to Japanese Patent Application No. 2019-036309, filed Feb. 28, 2019, the entireties of which are incorporated by reference herein.

TECHNICAL FIELD

The present invention relates to new uses of 3-phenylpropionic acid and 3-(4-hydroxyphenyl)propionic acid, that is, a use for inducing pili formation in bacterium of genus *Bifidobacterium* and a use for promoting intestinal colonization of the bacteria.

BACKGROUND ART

The genus *Bifidobacterium* is one of the bacteria that have colonized in the human intestine, and is known to bring various beneficial effects to a host human such as prevention of diarrhea, reduction of harmful bacteria and toxic compounds, immunomodulation, and anticarcinogenic activity (Non-Patent Literatures 1 to 3).

It has been presumed that the pili structure is involved in the interaction between the host and the bacteria (Non-Patent Literatures 4 and 5). It is known that the bacterium of genus *Bifidobacterium* has gene clusters involved in the pili formation. However, no pili structure has been confirmed in the bacterium of genus *Bifidobacterium* that has been isolated from human and cultured under general conditions.

3-Phenylpropionic acid is known to be a metabolite of phenylalanine produced by *Clostridium sporogenes*, which is an intestinal bacterium (Non-Patent Literature 6).

CITATION LIST

Non-Patent Literature

Non-Patent Literature 1: S. Fukuda et al., Nature, 2011, 469, 543-547.
Non-Patent Literature 2: S. Fanning et al., PNAS, 2012, 109 (6), 2108-2113.
Non-Patent Literature 3: Sivan A. et al., Science. 2015, 350 (6264), 1084-1089.
Non-Patent Literature 4: O'Connell Motherway et al., PNAS 2011, 108 (27), 11217-11222.
Non-Patent Literature 5: F. Turroni et al., PNAS 2013, 110 (27) 11151-11156.
Non-Patent Literature 6: S. R. Elsden, et al., Archives of Microbiology April 1976, 107 (3), 283-288.

SUMMARY OF INVENTION

Technical Problem

The present inventors have presumed that the bacterium of genus *Bifidobacterium* forms pili in the intestine, and assumed that the intestine has a substance that induces pili formation in the bacterium. The pili structure is presumed to promote the intestinal colonization of the bacterium, and therefore it is considered that such a substance has an intestinal colonization-promoting effect of the bacterium of genus *Bifidobacterium*, and may be useful for improving the intestinal microbiome.

In view of such a situation, the object of the present invention is to provide a method for inducing pili formation in the bacterium of genus *Bifidobacterium* and a method for promoting intestinal colonization of the bacterium.

Solution to Problem

The present inventors have intensively investigated to solve the above problems, and have found that pili formation is observed in the bacterium of genus *Bifidobacterium* cultured in a model culture imitating the intestinal tract. 3-Phenylpropionic acid has been identified as a substance that induces pili formation from the culture. Furthermore, it has been found that the bacterium of genus *Bifidobacterium* with pili formation induced enhances the adhesion to the substance constituting the intestinal epithelium, and it has been considered that 3-phenylpropionic acid can promote the intestinal colonization of the bacterium of genus *Bifidobacterium*. In addition, it has been found that 3-phenylpropionic acid, which is a metabolite of phenylalanine, and 3-(4-hydroxyphenyl)propionic acid, which is a metabolite of tyrosine, produced by the bacterium of genus *Clostridium* induce the pili formation in the bacterium of genus *Bifidobacterium*, and it has also been considered that the bacterium of genus *Clostridium* has a crosstalk relationship that can induce the pili formation in the bacterium of genus *Bifidobacterium* and promote the intestinal colonization thereof.

That is, one aspect of the present invention is a composition for inducing the pili formation in the bacterium of genus *Bifidobacterium*, the composition containing 3-phenylpropionic acid and/or 3-(4-hydroxyphenyl)propionic acid as an active ingredient.

In addition, another aspect of the present invention is a composition for promoting the intestinal colonization of the bacterium of genus *Bifidobacterium*, the composition containing 3-phenylpropionic acid and/or 3-(4-hydroxyphenyl) propionic acid as an active ingredient.

[Chemical Formula 1]

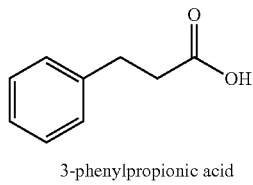

3-phenylpropionic acid

[Chemical Formula 2]

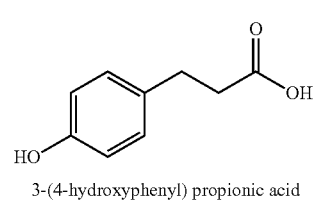

3-(4-hydroxyphenyl) propionic acid

In these aspects, the bacterium of genus *Bifidobacterium* is preferably *Bifidobacterium longum*.

In addition, the composition in these aspects is preferably a food and drink or a pharmaceutical product.

Another aspect of the present invention is the use of 3-phenylpropionic acid and/or 3-(4-hydroxyphenyl)propionic acid in the production of a composition for inducing the pili formation in the bacterium of genus *Bifidobacterium*.

Another aspect of the invention is the use of 3-phenylpropionic acid and/or 3-(4-hydroxyphenyl)propionic acid for inducing the pili formation in the bacterium of genus *Bifidobacterium*.

Another aspect of the invention is 3-phenylpropionic acid and/or 3-(4-hydroxyphenyl)propionic acid used for inducing the pili formation in the bacterium of genus *Bifidobacterium*.

Another aspect of the invention is a method for inducing the pili formation in the bacterium of genus *Bifidobacterium*, including administering to an animal 3-phenylpropionic acid and/or 3-(4-hydroxyphenyl)propionic acid.

Another aspect of the present invention is the use of 3-phenylpropionic acid and/or 3-(4-hydroxyphenyl)propionic acid in the production of a composition for promoting the intestinal colonization of the bacterium of genus *Bifidobacterium*.

Another aspect of the invention is the use of 3-phenylpropionic acid and/or 3-(4-hydroxyphenyl)propionic acid for promoting the intestinal colonization of the bacterium of genus *Bifidobacterium*.

Another aspect of the present invention is 3-phenylpropionic acid and/or 3-(4-hydroxyphenyl)propionic acid used for promoting the intestinal colonization of the bacterium of genus *Bifidobacterium*.

Another aspect of the invention is a method for promoting the intestinal colonization of the bacterium of genus *Bifidobacterium*, including administering to an animal 3-phenylpropionic acid and/or 3-(4-hydroxyphenyl) propionic acid.

Another aspect of the present invention is a composition for inducing the pili formation in the bacterium of genus *Bifidobacterium*, the composition containing a microorganism that produces 3-phenylpropionic acid and/or 3-(4-hydroxyphenyl)propionic acid.

Another aspect of the present invention is a composition for promoting the intestinal colonization of the bacterium of genus *Bifidobacterium*, the composition containing a microorganism that produces 3-phenylpropionic acid and/or 3-(4-hydroxyphenyl)propionic acid.

In these aspects, the microorganism is preferably the bacterium of genus *Clostridium*.

In these aspects, the bacterium of genus *Bifidobacterium* is preferably *Bifidobacterium longum*.

Another aspect of the present invention is an intestinal regulating composition containing the bacterium of genus *Bifidobacterium* and 3-phenylpropionic acid and/or 3-(4-hydroxyphenyl)propionic acid.

Another aspect of the present invention is a composition for improving the intestinal microbiome, the composition containing the bacterium of genus *Bifidobacterium* and 3-phenylpropionic acid and/or 3-(4-hydroxyphenyl)propionic acid.

Advantageous Effects of Invention

The present invention can induce the pili formation in the bacterium of genus *Bifidobacterium*, thereby promoting the intestinal colonization of the bacterium. The present invention can also lead to improvement of the intestinal microbiome to a state in which the bacterium of genus *Bifidobacterium* dominates.

BRIEF DESCRIPTION OF DRAWINGS

FIG. 1a: with addition of human stool, FIG. 1b: without addition of human stool

DESCRIPTION OF EMBODIMENTS

Figure 1:
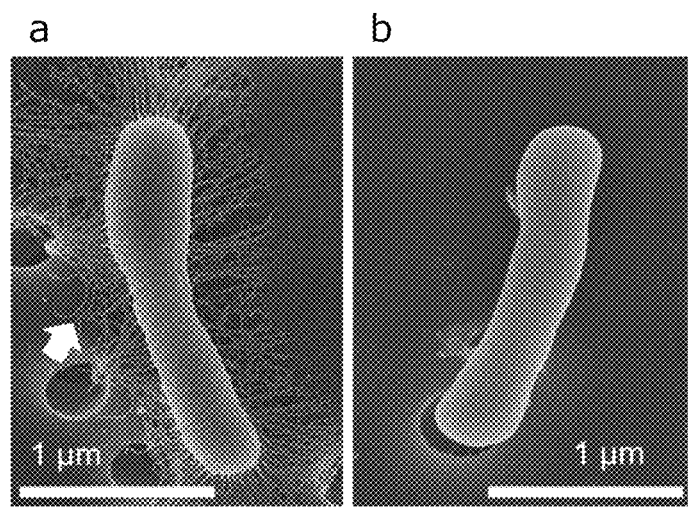
FIG. 1 is a transmission electron micrograph of *Bifidobacterium longum* cultured in an intestinal model (KUHIMM) culture solution in Test Example 1.

The present invention will be specifically described. However, the present invention is not limited to the following embodiments and can be freely changed within the scope of the present invention.

The composition of the present invention contains 3-phenylpropionic acid (also referred to as PPA) and/or 3-(4-hydroxyphenyl)propionic acid (also referred to as HPPA) as active ingredients. Of these, 3-phenylpropionic acid is preferably an active ingredient, from the viewpoint of the strength of the pili formation-inducing action in the bacterium of genus *Bifidobacterium*.

3-Phenylpropionic acid and 3-(4-hydroxyphenyl)propionic acid may be produced by known synthetic methods, or commercially available ones may be used.

In addition, the active ingredients of the composition of the present invention may be in the form of a microorganism that produces 3-phenylpropionic acid and/or 3-(4-hydroxyphenyl)propionic acid.

Preferable examples of such a microorganism include the bacterium of genus *Clostridium*, and more specifically, preferable examples include *Clostridium sporogenes* and *C. cadaveris*. In these bacteria, 3-phenylpropionic acid is produced as a metabolite of phenylalanine and 3-(4-hydroxyphenyl)propionic acid is produced as a metabolite of tyrosine.

When the composition of the present invention is in the aspect of such a microbial preparation, the composition is typically in a form including viable cells.

The amounts of 3-phenylpropionic acid and/or 3-(4-hydroxyphenyl)propionic acid in the composition of the present invention may be appropriately set depending on the aspect of the composition, are not particularly limited, and for example, the total amount is preferably 0.01% by mass or more with respect to the composition, and more preferably 0.1% by mass or more. The upper limits of the contents of 3-phenylpropionic acid and/or 3-(4-hydroxyphenyl)propionic acid are not particularly limited, and for example, the total amount may be 100% by mass or less.

The composition of the present invention can induce the pili formation in the bacterium of genus *Bifidobacterium*. The bacterium of genus *Bifidobacterium* is not particularly limited, and is preferably *Bifidobacterium longum*.

The pili of bacterium of genus *Bifidobacterium* is formed as a huge fiber by polymerization of FimA protein on the cell surface by sortase (SrtC and SrtA) and binding of FimB protein to the tip thereof (K. Suzuki et al., B. M. F. H., 2016, 35 (1), 19-27). As shown in the examples later, in the presence of 3-phenylpropionic acid and/or 3-(4-hydroxyphenyl)propionic acid, the expression of the gene involved in pili formation, specifically at least the gene encoding pili structural proteins (fimA, fimB) and the gene encoding the enzyme that polymerizes the structural protein (srtC) is enhanced, and thus pilus formation is induced.

The pili formation can be directly confirmed by, for example, observation of the cell surface of the bacterium of genus *Bifidobacterium* with a scanning electron microscope.

It can also be confirmed by a known method such as Western blotting with an antibody that recognizes proteins constituting pili, such as an anti-FimA antibody. When pili are formed, a band showing rudder-shaped pili is observed at a position of about 50 kDa to about 200 kDa or more, which is typically the molecular weight of the FimA monomer.

FimA, a major constituent protein of the pili in bacterium of genus *Bifidobacterium*, has lectin-like properties, and therefore this is considered to contribute to the adhesion of the bacterium to the intestinal epithelial cells via the pili. As shown in the test examples described later, the binding to the cells constituting the intestinal epithelium is more significant in the bacterium of genus *Bifidobacterium* with pili formation induced, as compared with the case where no pili formation is induced.

It is considered that improvement of the adhesion of the bacterium of genus *Bifidobacterium* to intestinal epithelial cells promotes the intestinal colonization of the bacterium. Herein, "colonization" includes that the amount of bacterium present in the intestine increases by adhesion to the intestinal epithelium as compared with the amount before ingestion (administration) of the composition, and the amount of the bacterium excreted from the intestine decreases as compared with that before ingestion (administration) of the composition.

Therefore, the composition of the present invention can promote the intestinal colonization of the bacterium of genus *Bifidobacterium*. Furthermore, it is expected that the intestinal microbiome is improved to a state in which the bacterium of genus *Bifidobacterium* dominates.

The subject to which the composition of the present invention is administered (ingested) is not particularly limited as long as it is an animal, but humans are preferable. In addition, the subject may be any of adults, children, infants, and newborns (including low-weight babies).

Another aspect of the present invention is the use of 3-phenylpropionic acid and/or 3-(4-hydroxyphenyl)propionic acid in the production of a composition for inducing the pili formation in the bacterium of genus *Bifidobacterium*.

Another aspect of the invention is the use of 3-phenylpropionic acid and/or 3-(4-hydroxyphenyl)propionic acid for inducing the pili formation in the bacterium of genus *Bifidobacterium*.

Another aspect of the invention is 3-phenylpropionic acid and/or 3-(4-hydroxyphenyl)propionic acid used for inducing the pili formation in the bacterium of genus *Bifidobacterium*.

Another aspect of the invention is a method for inducing the pili formation in the bacterium of genus *Bifidobacterium*, including administering to an animal 3-phenylpropionic acid and/or 3-(4-hydroxyphenyl)propionic acid.

Another aspect of the present invention is the use of 3-phenylpropionic acid and/or 3-(4-hydroxyphenyl)propionic acid in the production of a composition for promoting the intestinal colonization of the bacterium of genus *Bifidobacterium*.

Another aspect of the invention is the use of 3-phenylpropionic acid and/or 3-(4-hydroxyphenyl)propionic acid for promoting the intestinal colonization of the bacterium of genus *Bifidobacterium*.

Another aspect of the present invention is 3-phenylpropionic acid and/or 3-(4-hydroxyphenyl)propionic acid used for promoting the intestinal colonization of the bacterium of genus *Bifidobacterium*.

Another aspect of the invention is a method for promoting the intestinal colonization of the bacterium of genus *Bifidobacterium*, including administering to an animal 3-phenylpropionic acid and/or 3-(4-hydroxyphenyl) propionic acid.

Another aspect of the present invention is an intestinal regulating composition containing the bacterium of genus *Bifidobacterium* and 3-phenylpropionic acid and/or 3-(4-hydroxyphenyl)propionic acid.

Another aspect of the present invention is a composition for improving the intestinal microbiome, the composition containing the bacterium of genus *Bifidobacterium* and 3-phenylpropionic acid and/or 3-(4-hydroxyphenyl)propionic acid.

In the present invention, "regulating the intestine" means "regulating the intestinal microbiome and improving the disease related to the intestinal microbiome". As shown in examples described later, 3-phenylpropionic acid and/or 3-(4-hydroxyphenyl)propionic acid can colonize *Bifidobacterium* in the intestine, and therefore the composition of this aspect can reduce a so-called bad bacterium and improve the intestinal microbiome to a state in which the bacterium of genus *Bifidobacterium* dominates, thereby improving the disease related to the intestinal microbiome.

For example, it is known that in the intestinal microbiome, some bad bacteria may promote carcinogenesis by producing or activating mutagens and carcinogens, while some beneficial bacteria are useful for the prevention of cancer by the function of removing these substances, such as differentiation, inactivation, or adsorption. In addition, the study has also been reported, for example, showing that the intestinal microbiome is deeply involved in obesity and metabolic syndrome. Furthermore, there are reports suggesting that the intestinal microbiome is involved in psychiatric disorders such as autism and depression, responses to stress, and phenomena related to brain functions such as emotional behavior and learning.

Therefore, examples of "diseases related to the intestinal microbiome" include inflammatory diseases such as ulcerative colitis, functional gastrointestinal disorders such as IBS, functional constipation, and functional diarrhea, cancer of the intestinal system, metabolic syndrome, and neurological disorders. Examples of cancers of the intestinal system include duodenal cancer, small intestine cancer, and colorectal cancer. Examples of the colorectal cancer include cecal cancer, colon cancer, and rectal cancer. Examples of the metabolic syndrome include obesity (particularly, visceral fat obesity), hypertension, dyslipidemia, and diabetes. Examples of the neurological disorders include anxiety disorders, autism, and depression.

The ingestion (administration) timing of the composition of the present invention is not particularly limited, and can be appropriately selected according to the state of the subject for administration.

The intake (dose) of the composition of the present invention is appropriately selected depending on the age, sex, state, and other conditions of the subject for ingestion (administration). The intake of 3-phenylpropionic acid and/or 3-(4-hydroxyphenyl)propionic acid is preferably in the range of 100 to 1000 mg/day, more preferably 100 to 500 mg/day, and still more preferably 100 to 300 mg/day.

The composition can be administered once a day or in a plurality of doses regardless of the intake (dose) and duration.

The route of ingestion (administration) of the composition of the present invention may be oral or parenteral, and oral is preferable. In addition, examples of parenteral ingestion (administration) includes transdermal, intravenous injection, rectal administration, and inhalation.

After ingestion (administration), it is desirable that an effective amount or more of 3-phenylpropionic acid and/or 3-(4-hydroxyphenyl)propionic acid is maintained in the intestine.

When the composition of the present invention is taken orally, the aspect of food and drink is preferable.

The form and description of the food and drink are not particularly limited as long as the food and drink does not impair the effects of 3-phenylpropionic acid and/or 3-(4-hydroxyphenyl)propionic acid and can be ingested orally, and the food and drink can be produced by a common method with raw materials typically used for foods and drinks, except for containing 3-phenylpropionic acid and/or 3-(4-hydroxyphenyl)propionic acid.

Regardless of the forms such as liquid, paste, gel solid, and powder, examples of the food and drink include: tablets; liquid food (nutrition food for tube intake); wheat flour products such as bread, macaroni, spaghetti, noodles, cake mix, fried chicken seasoning mix, and bread crumbs; instant foods such as instant noodles, cup noodles, retort/cooked foods, canned foods, microwave foods, instant soups/stews, instant miso soup/soups, canned soups, freeze-dried foods, and other instant foods; agricultural processed products such as canned agricultural products, canned fruits, jams and marmalades, pickles, boiled beans, dried agricultural products, and cereals (processed grain products); processed marine products such as canned marine products, fish hams and sausages, paste products, marine delicacies, and tsukudani; livestock processed products such as livestock canned foods and pastes, and livestock ham and sausage; milk and dairy products such as processed milk, milk drinks, yogurts, fermented milk, lactic acid bacteria drinks, cheese, ice creams, formula milk powders, creams, and other dairy products; oils and fats such as butter, margarines, and vegetable oils; basic seasonings such as soy sauce, miso, sauces, processed tomato seasonings, mirin, and vinegar; combined seasonings and foods such as cooking mixes, curry ingredients, sauces, dressings, noodle soups, spices, and other complex seasonings; frozen foods such as ingredient frozen foods, semi-cooked frozen foods, and cooked frozen foods; confectionery such as caramel, candies, chewing gum, chocolate, cookies, biscuits, cakes, pies, snacks, crackers, Japanese confectionery, rice confectionery, bean confectionery, dessert confectionery, jelly, and other confectionery; favorite drinks such as carbonated drinks, natural fruit juices, fruit juice drinks, soft drinks with fruit juice, fruit meat drinks, fruit drinks with fruit grains, vegetable drinks, soy milk, soy milk drinks, coffee drinks, tea drinks, powder drinks, concentrated drinks, sports drinks, nutritional drinks, alcoholic drinks, and other favorite drinks, and other commercial foods such as baby foods, Furikake, and Ochazuke Nori; milk powder for childcare; enteral nutritional foods; and functional foods (foods for specified health use, nutritionally functional foods).

In addition, the food and drink can also be used as feed as an aspect of food and drink. Examples of the feed include pet food, livestock feed, and fish feed.

The form of the feed is not particularly limited, and in addition to 3-phenylpropionic acid and/or 3-(4-hydroxyphenyl)propionic acid, the feed may contain: for example, cereals such as corn, wheat, barley, rye, and milo; vegetable oil cakes such as soybean oil cake, rapeseed oil cake, palm oil cake, and flax oil cake; bran such as wheat bran, barley bran, rice bran, defatted rice bran; manufactured cake such as corn gluten meal and corn jam meal; animal feeds such as fish meal, skim milk powder, whey, yellow grease, and tallow; yeasts such as torula yeast and brewer's yeast; mineral feeds such as tricalcium phosphate and calcium carbonate; oils and fats; simple amino acids; and sugars.

When the composition of the present invention is in the aspect of foods and drinks (including feeds), the amounts of 3-phenylpropionic acid and/or 3-(4-hydroxyphenyl)propionic acid included therein are not particularly limited and may be appropriately selected, and for example, the total amount is preferably 0.01% by mass or more with respect to the food and drink, and more preferably 0.1% by mass or more. The upper limits of the contents of 3-phenylpropionic acid and/or 3-(4-hydroxyphenyl)propionic acid are not particularly limited, and for example, the content may be preferably 70% by mass or less, more preferably 40% by mass or less, and still more preferably 5% by mass or less.

When the composition of the present invention is in the aspect of foods and drinks (including feeds), the food and drink labeled for the purpose of promoting the intestinal colonization of the bacterium of genus *Bifidobacterium* can be provided and sold. In addition, 3-phenylpropionic acid and/or 3-(4-hydroxyphenyl)propionic acid according to the present description can be used for the production of these foods and drinks.

As long as such "labeling" act includes all acts for informing the consumer of the above use and the label describes the expression such that the above use can be recalled or analogized, all of the labels correspond to the "labeling" act of the present invention regardless of the purpose of the label, the content of the label, and the object or medium to be labeled.

In addition, the "labeling" preferably includes an expression that allows the consumer to directly recognize the above use. Specific examples thereof include: the acts of transferring, delivering, or displaying and importing for transferring or delivering a food-and-drink related product or a packaging thereof with the above use described; and the acts of describing the above use in advertisements, price lists, or transaction documents and then displaying or distributing, or describing the above use in the information including these contents and then providing by an electromagnetic method (for example, Internet).

Whereas, the label is preferably approved by, for example, the government as the content of the label (for example, a label approved based on various systems established by the government and expressed in the aspect based on such approval). In addition, such a label content is preferably attached to packaging, containers, catalogs, pamphlets, promotional materials such as POP at sales sites, and other documents.

In addition, "labeling" includes labels such as health foods, functional foods, enteric nutritional foods, special purpose foods, health functional foods, specified health foods, nutritional functional foods, functional display foods, and non-medicinal products. Of these, particularly, the label approved by the Consumer Affairs Agency includes a label approved by a system related to specified health foods, nutritional functional foods, or functional display foods, or a system similar to these. Specific examples thereof can include a label as specified health foods, a label as specified health foods with conditions, a label describing that the structure and function of the body are affected, a label of reducing the risk of illness, and a label of the functionality based on scientific evidence, and more specifically, typical examples thereof are a label as specified health foods stipulated in the Cabinet Office Ordinance (Cabinet Office Ordinance No. 57 of August 31, Heisei 21) regarding permission for special use labeling prescribed in the Health Promotion Law (particularly the labeling for health use) and a label similar to this.

Examples of such a label include "a person who wants to increase bifidobacteria" and "for improving the intestinal microbiome".

The composition of the present invention can also be in the aspect of a drug.

The route of administration of the drug may be oral or parenteral, and oral is preferable. In addition, parenteral administration includes transdermal, intravenous injection, rectal administration, and inhalation.

The form of the drug can be appropriately formulated into a desired dosage form according to the administration method. For example, in the case of oral administration, the formulation can include solid dosage forms such as powders, granules, tablets, and capsules; and liquid dosage forms such as solutions, syrups, suspensions, and emulsions. In addition, in the case of parenteral administration, the formulation can include a suppository, an ointment, and an injection.

After administration, it is desirable that an effective amount or more of 3-phenylpropionic acid and/or 3-(4-hydroxyphenyl)propionic acid is maintained in the intestine, and therefore preferable oral preparations include an enteric capsule preparation and sugar-coated tablets with acid resistance.

In formulation, in addition to 3-phenylpropionic acid and/or 3-(4-hydroxyphenyl)propionic acid, components such as excipients, pH adjusters, colorants, and flavoring agents that are typically used in formulation can be used. In addition, other medicinal properties, or known or future ingredients having an intestinal microbiome-improving action can be used in combination.

In addition, formulation can be performed by a known method as appropriate depending on the dosage form. In formulation, a formulation carrier may be blended and formulated as appropriate.

Examples of the excipients include: sugar derivatives such as lactose, sucrose, glucose, mannitol, and sorbitol; starch derivatives such as corn starch, potato starch, α-starch, dextrin, and carboxymethyl starch; cellulose derivatives such as crystalline cellulose, hydroxypropyl cellulose, hydroxypropylmethyl cellulose, carboxymethyl cellulose, and carboxymethyl cellulose calcium; gum arabic; dextran; pullulan; silicate derivatives such as light anhydrous silicic acid, synthetic aluminum silicate, and magnesium metasilicate aluminate; phosphate derivatives such as calcium phosphate; carbonate derivatives such as calcium carbonate; and sulfate derivatives such as calcium sulfate.

In addition to the above excipients, examples of the binder include: gelatin; polyvinylpyrrolidone; and macrogol.

In addition to the above excipients, examples of the disintegrant include chemically modified starch or cellulose derivatives such as croscarmellose sodium, carboxymethyl starch sodium, and crosslinked polyvinylpyrrolidone.

Examples of the lubricant include: talc; stearic acid; metal stearate salts such as calcium stearate and magnesium stearate; colloidal silica; waxes such as pea gum and gay wax; boric acid; glycol; carboxylic acids such as fumaric acid and adipic acid; sodium carboxylic acid salts such as sodium benzoate; sulfates such as sodium sulfate; leucine; lauryl sulfates such as sodium lauryl sulfate and magnesium lauryl sulfate; silicic acids such as anhydrous silicic acid and silicic acid hydrate; and starch derivatives.

Examples of the stabilizer include: paraoxybenzoic acid esters such as methylparaben and propylparaben; alcohols such as chlorobutanol, benzyl alcohol, and phenylethyl alcohol; benzalconium chloride; acetic anhydride; and sorbic acid.

Examples of the flavoring agent include sweeteners, acidulants, and flavors.

Examples of the carrier used in the case of a liquid preparation for oral administration include a solvent such as water.

When the composition of the present invention is in the aspect of the drug, the amounts of 3-phenylpropionic acid and/or 3-(4-hydroxyphenyl)propionic acid included therein are not particularly limited and may be appropriately selected, and for example, the total amount is preferably 40% by mass or more with respect to the drug, more preferably 50% by mass or more, and still more preferably 97% by mass or more. The upper limits of the contents of 3-phenylpropionic acid and/or 3-(4-hydroxyphenyl)propionic acid are not particularly limited, and for example, the contents may be 100% by mass or less.

The timing of administration of the drug of the present invention is not particularly limited, for example, before meals, after meals, between meals, and before bedtime.

Examples

Hereinafter, the present invention will be described in more detail using examples, but the present invention is not limited to these examples.

<Test Example 1> Confirmation of Pili Formation in Intestinal Model Culture

*Bifidobacterium longum* 1-1 strain was cultivated in GAM broth, 1 mL of the bacterial solution obtained by preparing the culture solution at $OD_{600}$=0.1 was placed in a dialysis membrane, and anaerobic culture was performed at 37° C. for 24 hours while controlling with 1M $Na_2CO_3$ solution so that the pH did not drop below 6 in a single-batch anaerobic culture system (KUHIMM, R. Takagi et. al., PLoS One. 2016, 11 (8): e0160533., D. Sasaki et. al., Sci. Rep. 2018, 8

(1): 435). 100 μL of a human fecal solution prepared in advance to 10% (w/v) with physiological saline was added to the medium of the test group, and was not added to the negative control group.

When the cultured bacterium was fixed with osmium oxide and observed with a transmission electron microscope, large fiber-shaped pili were observed in the case of culturing with addition of human feces (FIG. 1).

In addition, when a transcriptome analysis was performed on the *Bifidobacterium longum* 1-1 strain in the test group cultured with the addition of human feces, clusters including the fimA, fimB, and srtC genes had the expression enhanced by 2-fold or more as compared with the negative control group.

<Test Example 2> Identification of Pili Formation-Inducing Substance

KUHIMM culture solution (900 mL) containing human feces used in Test Example 1 was fractionated in the order of MilliQ water, 50% methanol, and 100% methanol (250 mL of each) with an activated carbon column (resin volume: 45 mL). Of each fraction, 100 μL was collected in another container, dried under reduced pressure, and then redissolved in 50 μL of MilliQ water. Subsequently, the *Bifidobacterium longum* 1-1 strain was cultured in GAM medium, and 50 μL of the redissolved solution of the above fraction was added to 1 mL of the bacterial solution obtained by adjusting the above culture solution at $OD_{600}$=0.1, and culture was performed at 37° C. for 24 hours. After culture, the cells were collected by centrifugation (4000×g, 5 minutes). The cells were treated with an extract containing mutanolysin and lysozyme (reference composition: extraction buffer (50 mM Tris-HCl (pH 7.0), 40% (w/v) sucrose, 0.1 mg(w/v) lysozyme, 25 U mutanolysin (Sigma-Aldrich, M9901), cOmplete (Roche)) to fractionate the cell surface fraction including pili. Subsequently, the protein was concentrated by trichloroacetic acid precipitation and subjected to SDS-PAGE. After transfer to a PVDF membrane, Western blotting with an anti-FimA antibody was performed, and the pili signal was detected to evaluate the pili induction. The pili induction was observed in the fraction eluted with 100% methanol.

Furthermore, the fraction was fractionated and purified by HPLC (column: PEGASIL ODS SP100 φ20×250 mm, solvent conditions: 15 to 55% $CH_3CN/H_2O$-0.1% $HCO_2H$ 40 min gradient, flow rate: 6.0 mL/min, detection: UV 210 nm), and elution peaks (retention time 38 min) in which the pili induction was observed were repeatedly fractionated. Subsequently, the collected solution was dried under reduced pressure to obtain the desired active substance with a yield of 4.8 mg. The structure determination of this substance by mass spectrometry and NMR analysis identified that the compound included in the fraction was 3-phenylpropionic acid.

In addition, as a result of anaerobic culturing of the *Bifidobacterium longum* 1-1 strain at 37° C. for 24 hours on GAM agar medium containing 3-phenylpropionic acid (final concentration 0.01, 0.1, 0.5, 1.0, 2.5, 10, 20, 40, or 80 μg/mL), it was confirmed that 3-phenylpropionic acid induced pili polymerization dose-dependently. Particularly, addition at a concentration of more than 0.1 μg/mL to the medium clearly induced the pili formation.

<Test Example 3> Confirmation of Pili-Formation Induction of PPA

*Bifidobacterium longum* 1-1 strain was anaerobically cultured at 37° C. for 24 hours on GAM agar medium containing 10 μg/mL of 3-phenylpropionic acid.

Figure 2:
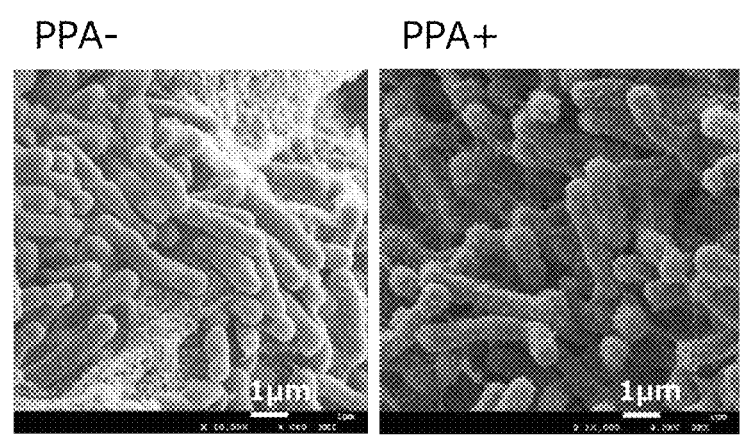
FIG. 2 is a scanning electron micrograph of cultured *Bifidobacterium longum* in Test Example 3. PPA−: without addition of 3-phenylpropionic acid, PPA+: addition of 3-phenylpropionic acid

When the cultured bacterium was observed with a scanning electron microscope, large fiber-shaped pili were observed in the case of culturing with addition of 3-phenylpropionic acid (FIG. 2).

As a result of analyzing the expression status of the pili formation-related gene by quantitative reverse transcription PCR for the bacterium in which the pili formation was confirmed, it was found that the expression of the cluster including the fimA, fimB, and srtC genes was enhanced by about 3 to 5-fold as compared with the negative control group.

Furthermore, the adhesion of the cultured cells to the human intestinal epithelial cell line (Caco-2 or HT29-MTX) was evaluated. Specifically, the *Bifidobacterium longum* 1-1 strain was cultured on GAM medium containing 10 μg/mL of PPA at 37° C. for 15 hours. The cells were centrifuged (4000×g, 1 min, 4° C.), collected, and suspended in Dulbecco's modified Eagle's medium (DMEM) at $OD_{600}$=0.5. 0.2 mL of this bacterial solution was added to a chamber slide glass in which HT29-MTX or Caac-2 cells had been cultured in a single layer, and was allowed to stand at 37° C. for 2 hours. After washing with DMEM medium, *Bifidobacterium longum* adhered with 4% paraformaldehyde was fixed and stained with crystal violet. The number of bacteria per well was counted under a microscope.

Figure 3:
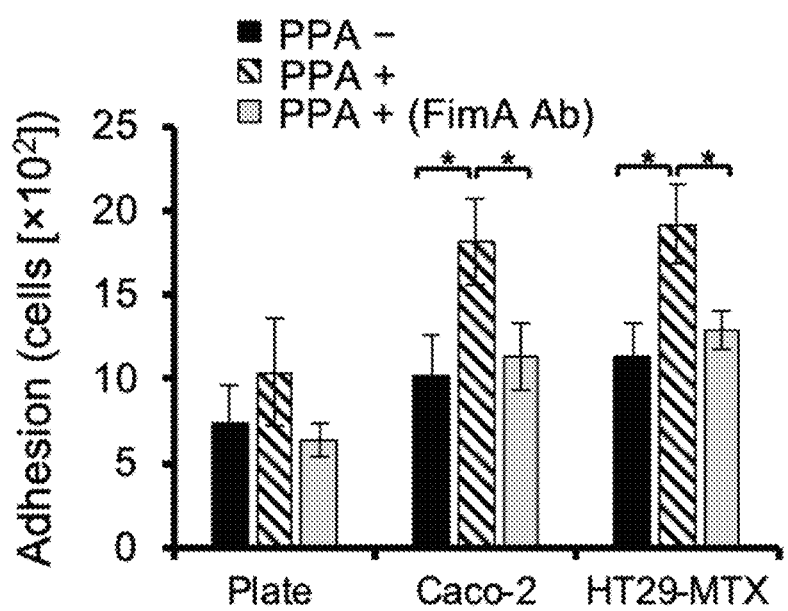
FIG. 3 is a graph showing the adhesion of cultured *Bifidobacterium longum* to a human intestinal epithelial cell line in Test Example 3. From the left of each group, PPA−: without addition of 3-phenylpropionic acid, PPA+: with addition of 3-phenylpropionic acid, PPA+ (FimA Ab): with addition of 3-phenylpropionic acid and with addition of anti-FimA antibody

It was confirmed that the adhesion was significantly larger in the presence of 3-phenylpropionic acid than in the absence thereof, and was significantly reduced due to inhibition by the anti-FimA antibody (FIG. 3).

These results found that 3-phenylpropionic acid has an action of inducing the pili formation in the *Bifidobacterium longum*, and that pili are a factor of adhesion to the intestinal epithelium.

<Test Example 4> Pili Formation of Bacterium of Genus *Bifidobacterium* Co-Cultured with PPA-Metabolizing Enzyme-Deficient Bacterium of Genus *Clostridium*

According to the method of Dodder et al. (ClosTron-mediated engineering of *Clostridium* (PMID: 22750794), The ClosTron: Mutagenesis in *Clostridium* refined and streamlined (PMID: 19891996)), the ClosTron cassette was inserted into the fldC (PMID: 29168502) of the *Clostridium sporogenes* ATCC11437 strain to destroy the fldC subunit. fldC is a gene encoding the PPA-metabolizing enzyme, phenyllactic dehydratase in *Clostridium sporogenes*. As a result of culturing this fldC-deficient *Clostridium sporogenes* on GAM medium for 36 hours, it was confirmed that PPA was not detected in the culture supernatant.

The fldC-deficient or wild-type strain of *Clostridium sporogenes* and the *Bifidobacterium longum* 1-1 strain were co-cultured on GAM culture medium for 24 hours.

Figure 4:
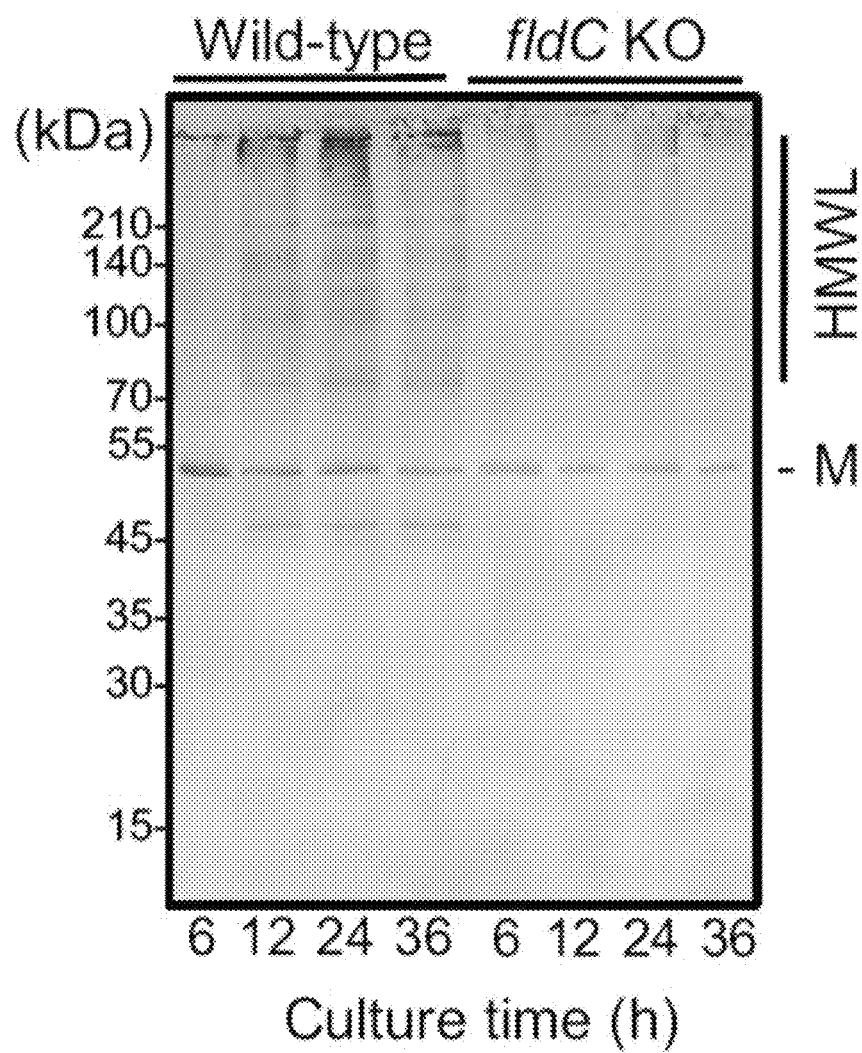
FIG. 4 is a photograph of Western blotting showing the pili formation in *Bifidobacterium longum* co-cultured with *Clostridium sporogenes* in Test Example 4.

Western blotting was performed on the cultured *Bifidobacterium longum* in the same manner as in Test Example 1, and no pili formation was observed in the case of co-culturing with the fldC-deficient strain of *Clostridium sporogenes* (FIG. 4).

<Test Example 5> Confirmation of Pili-Formation Induction of Aromatic Amino Acid and Metabolite Thereof

*Bifidobacterium longum* 1-1 strain was anaerobically cultured at 37° C. for 24 hours on GAM agar medium containing 10 μg/mL of aromatic amino acids or the amino acid metabolite produced by *Clostridium sporogenes*. Substances added include: phenylalanine and metabolites thereof such as phenylalanine, phenyllactic acid, phenylacrylic acid, or 3-phenylpropionic acid; tyrosine and metabolites thereof such as tyrosine, 4-hydroxyphenyllactic acid, 4-hydroxyphenyl acrylic acid, or 3-(4-hydroxyphenyl)propionic acid;

and tryptophan and metabolites thereof such as tryptophan, indole lactic acid, indole acrylic acid, or 3-(indole)propionic acid.

Figure 5:
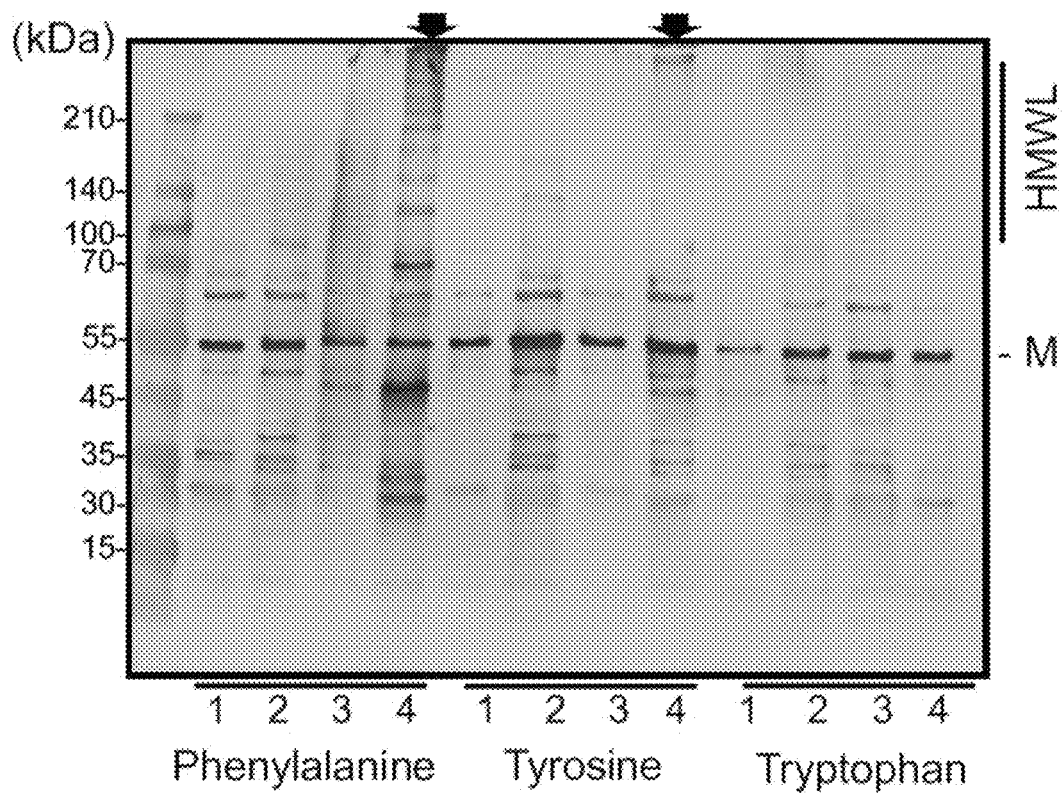
FIG. 5 is a photograph of Western blotting showing the pili formation in *Bifidobacterium longum* cultured in GAM culture medium added with an amino acid metabolite in Test Example 5. Phenylalanine and metabolites thereof including 1: phenylalanine, 2: phenyllactic acid, 3: phenylacrylic acid, and 4: 3-phenylpropionic acid; tyrosine and metabolites thereof including 1: tyrosine, 2: 4-hydroxyphenyllactic acid, 3: 4-hydroxyphenyl acrylic acid, and 4: 3-(4-hydroxyphenyl)propionic acid; and tryptophan and metabolites thereof including 1: tryptophan, 2: indole lactic acid, 3: indole acrylic acid, and 4: 3-(indole)propionic acid.

As described in Test Example 1, as a result of extracting the surface protein from the culture solution of the cultured *Bifidobacterium longum* and performing Western blotting, the pili formation was observed in the case of culturing with addition of 3-phenylpropionic acid. In addition, in the case of culturing with addition of 3-(4-hydroxyphenyl)propionic acid, the pili formation was observed although less significant than in the former case (FIG. 5).

<Test Example 6> Confirmation of Pili Formation in Bacterium of Genus *Bifidobacterium* in Mouse Ingesting Bacterium of Genus *Clostridium*

*Clostridium sporogenes* ATCC 11437 strain and *Bifidobacterium longum* 1-1 strain (BL+CS group, n=4) or *Bifidobacterium longum* 1-1 strain (BL group, n=5) were administered to a germ-free mouse once on the first day. The amount of *Clostridium sporogenes* ATCC11437 strain administrated was $2.0 \times 10^7$ CFU/100 μL, and the amount of *Bifidobacterium longum* 1-1 strain administered was $3.4 \times 10^7$ CFU/100 μL. Throughout the experimental period, the number of bacteria in the feces was measured weekly by quantitative PCR according to the method of T. Matsuki et al., Appl. Environ. Microbiol. (2004) 70 (1): 167-73. The primer used to detect *Bifidobacterium longum* was BiLON-1/BiLON-2 (T. Matsuki et al., Appl. Environ. Microbiol. (2004) 70 (1): 167-173), and the primer used to detect *Clostridium sporogenes* was Sporog-F/Sporog-R (S. Morandi et al., Anaerobe. 2015, 34: 44-49).

In the BL+CS group, it was confirmed that the *Clostridium sporogenes* stably formed colonies throughout the experimental period. In addition, in the BL+CS group, PPA in the feces was detected at an average of 21 to 38 μM, but in the BL group, no PPA was detected.

Figure 6:
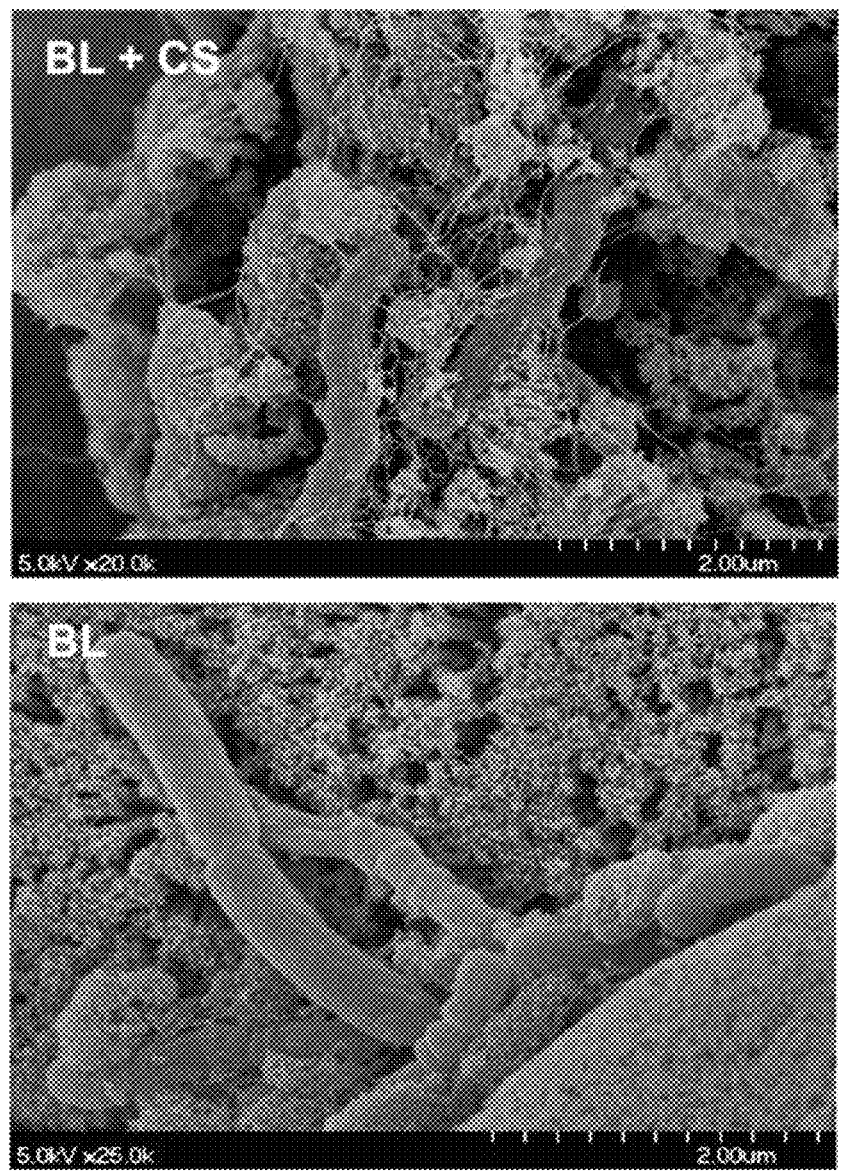
FIG. 6 is a scanning electron micrograph of *Bifidobacterium longum* in feces of a gnotobiote mouse in Test Example 6. BL: *Bifidobacterium longum* inoculated mouse, BL+CS: *Bifidobacterium longum* and *Clostridium sporogenes* inoculated mouse

As a result of dissecting the mouse 7 weeks after the start of administration and observing the *Bifidobacterium longum* adhered to the intestinal epithelium of the mouse in each group with a scanning electron microscope, large fiber-shaped pili were observed in the BL+CS group (FIG. 6).

In addition, 100 mg of mouse feces was collected, completely suspended in an extract including 300 μL of mutanolysin and lysozyme, and incubated at 37° C. for 3 hours. Centrifugation (8000×g, 10 min, 4° C.) was performed, and 200 μL of the supernatant was collected. Subsequently, the protein was concentrated by trichloroacetic acid precipitation and subjected to SDS-PAGE. After transfer to a PVDF membrane, Western blotting with an anti-FimA antibody was performed to detect a pili signal. In the BL+CS group, a FimA polymer was detected and pili formation was observed.

<Test Example 7> Evaluation of Adhesion of Bacterium of Genus *Bifidobacterium* to Intestinal Tract of Mouse The mouse containing *Clostridium sporogenes* ATCC11437 strain and *Bifidobacterium longum* 1-1 strain (BL+CS group, n=4) or *Bifidobacterium longum* 1-1 strain (BL group, n=5) was dissected 7 weeks after the start of the administration. The cecum was washed with saline and the bacteria adhering to the intestinal epithelium were collected with a scraper. The numbers of *Clostridium sporogenes* and *Bifidobacterium longum* were measured by qPCR in the same manner as in Test Example 6.

Figure 7:
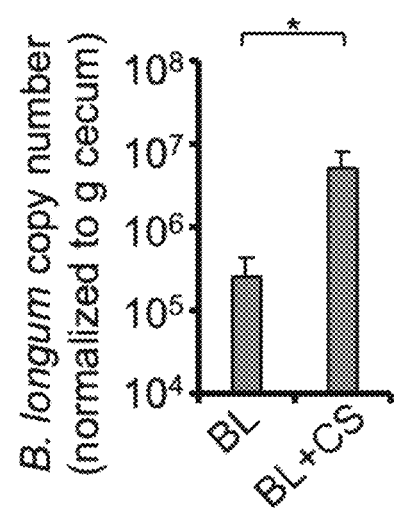
FIG. 7 is a graph showing the number of *Bifidobacterium longum* on the cecal mucus of a gnotobiote mouse in Test Example 7. BL: *Bifidobacterium longum* inoculated mouse, BL+CS: *Bifidobacterium longum* and *Clostridium sporogenes* inoculated mouse

The result is shown in FIG. 7. In the BL+CS group in which pili were observed, a significant increase (*$p<0.05$) in the number of the bacteria adhering to the cecal epithelium of the mouse was observed as compared with the BL group.

The invention claimed is:

1. A method for inducing pili formation in *Bifidobacterium longum* present in the intestines of an animal in need of increased pili formation in said bacterium,
    wherein said method comprises orally administering to the animal 3-phenylpropionic acid and/or 3-(4-hydroxylphenyl) propionic acid, wherein said administering results in an increase in pili formation in the *Bifidobacterium longum*, and as a result of said increase, intestinal colonization in the animal by said bacterium is increased.

2. The method of claim 1, further comprising the prior step of formulating 3-phenylpropionic acid and/or 3-(4-hydroxyphenyl) propionic acid with other ingredients.

* * * * *